United States Patent [19]

Oppici et al.

[11] 4,021,426
[45] May 3, 1977

[54] PROCESS FOR PREPARING 6-AMINOPENICILLANIC ACID, 7-AMINOCEPHALOSPORANIC ACID AND ITS DERIVATIVES AT THE 3-POSITION

[75] Inventors: Ernesto Oppici; Anacleto Gianantonio, both of Milan, Italy

[73] Assignee: Gruppo Lepetit S.p.A., Milan, Italy

[22] Filed: July 17, 1975

[21] Appl. No.: 596,699

[30] Foreign Application Priority Data

Aug. 7, 1974 United Kingdom ............ 34754/74

[52] U.S. Cl. .................. 260/243 C; 260/239.1; 260/306.7 C
[51] Int. Cl.² ............. C07D 501/04; C07D 499/08
[58] Field of Search ...... 260/239.1, 243 C, 306.7 C

[56] References Cited

OTHER PUBLICATIONS

Flynn, "Cephalosporins & Penicillins," pp. 56–73, (1972).
Murphy et al., J. Org. Chem., vol. 35, pp. 2429–2430, (1970).

Primary Examiner—Gerald A. Schwartz
Attorney, Agent, or Firm—Theodore Post; C. Kenneth Bjork

[57] ABSTRACT

A process for preparing 6-APA and 7-ACA and derivatives therefore is disclosed wherein a penicillin or cephalosporin substrate is reacted with a molar excess of an oxalyl halide of the formula halCOCOhal whereby the COOM group of the substrate, wherein M represents hydrogen, metal or ammonium cations, is transformed into the group COOCOCOhal.

14 Claims, No Drawings

PROCESS FOR PREPARING 6-AMINOPENICILLANIC ACID, 7-AMINOCEPHALOSPORANIC ACID AND ITS DERIVATIVES AT THE 3-POSITION

The present invention is concerned with a new and useful method for splitting the group R—CO from compounds of the general formula

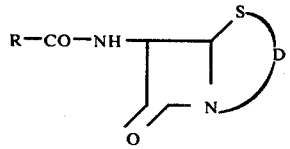

wherein D may be the group

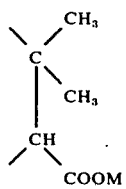

or the group

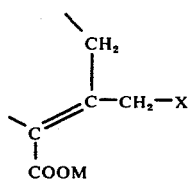

In these groups the carbon atom bearing the substituent COOM is linked to the nitrogen atom of the β-lactam ring.

It is understandable that when D represents the group

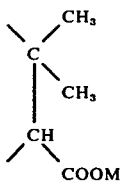

the compounds of the formula I are 6-acylaminopenicillanic acid derivatives of formula

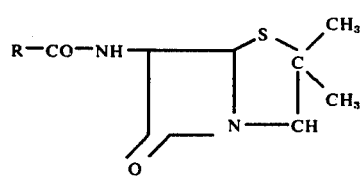

and that when D represents the group

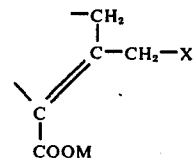

the compounds of formula I are 7-acylaminocephalosporanic acid derivatives of formula

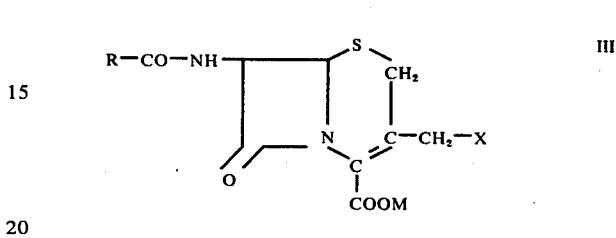

Accordingly the invention provides a new and useful method for preparing the 6-aminopenicillanic acid and derivatives at the 3-position of the 7-aminocephalosporanic acid, said compounds being represented by the following general formula

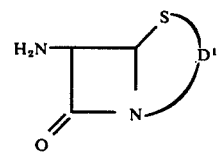

wherein $D^1$ may be the group

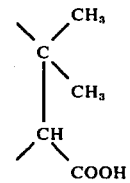

or the group

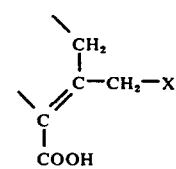

wherein the carbon atom bearing the carboxy group is linked to the nitrogen atom of the β-lactame ring.

In the above compounds of formulas I, II and III and in the moieties

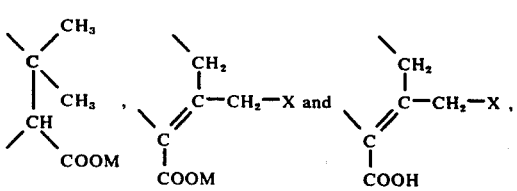

M represents hydrogen or metal or ammonium cations, X is a group selected from hydrogen, hydroxy, sulfhydryl, halo, azido, cyano, ($C_{1-6}$) alkoxy, ($C_{2-6}$) alkanoyloxy, carbamoyloxy, ($C_{1-6}$) alkylcarbamoyloxy, aryloxy, aralkyloxy, aroyloxy, arylalkanoyloxy wherein the aromatic portion is represented by a phenyl or naphthyl radical optionally substituted with ($C_{1-4}$) alkyl, ($C_{1-4}$) alkoxy, halo and nitro groups and the alkyl or alkanoyl portions contain from 1 to 4 carbon atoms, tri-($C_{1-4}$) alkylammonio, pyridinio, ($C_{1-4}$) alkyl substituted pyridinio, a group —S—Y or

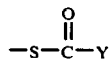

wherein Y stands for ($C_{1-6}$) alkyl, ($C_{2-6}$) alkanoyl, aryl and aralkyl as above defined, a 5–7 membered heterocyclic ring containing O, N and S and optionally substituted with ($C_{1-4}$) alkyl, hydroxy, hydroxy ($C_{1-4}$) alkyl or trifluoromethyl, such as, for instance thiazole, isothiazole, oxazole, isoxazole, 1,3,4-thiadiazole, 1,2,4-thiadiazole, 1,2,5-thiadiazole, 1,3,4-oxadiazole, 1,2,4-oxadiazole, 1,2,5-oxadiazole, 1,2,4-triazole, 1,2,3-triazole tetrazole, pyridine, pyridazine, pyrimidine, and pyrazine;

R is a member of the class consisting of:
a. alkyl of 2 to 8 carbon atoms;
b. a group

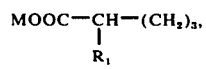

wherein M is defined as above and $R_1$ is hydrogen, amino or a protected amino group;
c. a group

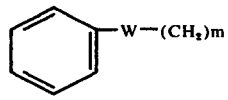

wherein W represents O, S or a carbon-carbon bond, and m is an integer from 0 to 3, with the proviso that when W is oxygen or sulfur, m is different from zero;
d. a group

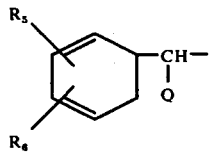

wherein Q stands for hydrogen, hydroxy or amino and $R_5$ and $R_6$ are independently selected from hydrogen, hydroxy, amino or halo;
e. a group

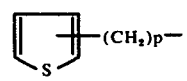

wherein p is an integer from 1 to 3. With the term "protected amino group" it is intended an aminic function protected by a group which is not effected by the hereinbelow described reaction conditions which are employed for splitting the moiety R—CO. Examples of protecting groups are acyl radicals deriving from mono- or di-carboxylic acids of 2 to 8 carbon atoms optionally substituted with halogen atoms, benzoyl, phenyl and benzoyl carrying 1 to 3 substituents independently selected from halo, nitro and cyano, phenacetyl, benzyloxycarbonyl, tert-butoxycarbonyl, ($C_{5-7}$) cycloalkyloxy carbonyl, benzenesulfonyl, toluenesulfonyl, phenacylsulfonyl, a group representable by the formula

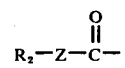

wherein Z is O or NH and $R_2$ is ($C_{1-6}$) alkyl or the group

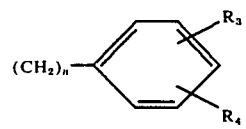

wherein n is an integer from 0 to 6 and $R_3$ and $R_4$ independently represent hydrogen, halogen, nitro, ($C_{1-6}$) alkyl, ($C_{1-6}$) alkoxy.

The process of the invention, which in its main aspects is carried out at a temperature between −10° and −60° C comprises as the first and inventive step the protection of the carboxylic group on the heterocyclic portion of the compounds of formula I, II and III by reacting the selected compound with an oxalyl halide such as for instance, oxalyl chloride or oxalyl bromide, being oxalyl chloride the more preferred one. Accordingly, the group COOM is readily transformed into the corresponding group COO—COCOhal, wherein hal stands for a halogen atom, preferably chlorine. The use of oxalyl chloride as protecting agent of the carboxy group is not known from the chemical literature: it is rather described and employed as halogenating agent, see for instance C. F. Murphy and R. E. Koehler, Jour. Org. Chem. 35, 2429, 1970, where it is said that oxalyl chloride displays its chlorinating action at a temperature of 0°–10° C. On the contrary, we have surprisingly found that by operating within the above indicated temperature range, oxalyl chloride may act as a protecting agent without any chlorinating effect on the reaction substrate.

After protection of the group, the removal of the R—CO radical is performed as described in the art, i.e. the selected substrate is treated with a halogenating agent, such as, for instance, phosphorus pentahalides, to obtain the corresponding iminohalide which is in turn reacted with an appropriate alcohol to give an iminoether: the iminoether is then hydrolyzed according to the known procedures for hydrolyzing said classes of substances.

During this last reaction steps also the hydrolysis of the group —COO—COCOhal takes place, so that 6-aminopenicillanic acid or 7-aminocephalosporanic acid or its derivatives with various substituents at the 3-position are practically recovered directly from the reaction mixture in almost quantitative yields.

It is known from the literature concerning penicillins, cephalosporins and derivatives thereof (Cephalosporins and Penicillins, chapter 2, page 27, Academic Press, New York and London, 1972), that the hydrolysis of the acylamino group at the 6- or 7- position, depending on whether substrates deriving from penicillins or cephalosporins are respectively involved, is a quite difficult problem also for a skilled technician, which requires strictly controlled reaction conditions, as many undesirable side-reactions may take place owing to lability of the substrates. Direct acid hydrolisis of cephalosporins C or benzylpenicillin as recovered from the fermentation broths is practically unsuccessful or gives very poor overall yields (lower than 1%). On the other hand, useful procedures for hydrolizing the acylamino groups at the 6- or 7-positions, which can be employed also on industrial scale, are undesirable as 6-aminopenicillanic acid, 7-aminocephalosporanic acid or its derivatives at the 3-position are very important intermediate products for preparing a lot of "semi-synthetic" penicillins and cephalosporins with very interesting antimicrobial properties.

A general method for the cleavage of the amidic bond of cephalosporins derivatives is that described in Belgian Pat. No. 628.494; this method, which proved to run also with penicillins deriving substrates comprises the following steps:

a. transformation of the amidic group into iminohalide;

b. subsequent transformation of the iminohalide into iminoether;

c. hydrolytic cleavage of the iminoether.

This process may provide 6-aminopenicillanic acid, 7-aminocephalosporanic acid or its derivatives with various substituents at the 3-position in good yields owing to the mild conditions which do not alter the very labile heterocyclic system, but this practically occurs only if the carboxy group on the heterocyclic portion of the selected substrate is blocked by an appropriate protecting agent, to avoid its transformation into carbonyl halide during the step concerned with the formation of the iminohalide. It is therefore clear that the key-passage which permits to obtain the desired end products in good yields is represented by the protection of the carboxylic group at issue and it is understandable as well that the choice of the appropriate protecting agent is rather critical for a good reaction proceeding. Several methods for protecting the carboxy group on the heterocyclic portion of penicillin or cephalosporin derivatives are described in the literature, but none of them is devoid of practical disadvantage, so that the so far known processes for preparing 6-aminopenicillanic or 7-aminocephalosporanic acid, or the derivatives at the 3-position of 7-aminocephalosporanic acid present several difficulties when carried out on industrial scale.

Thus, for instance, the protection by formation of esters both organic and inorganic, as described in U.S. Pat. No. 3,697,515 and subsequent hydrolysis of the 6 or 7-acylamino group according to Belgian Pat. No. 628,494 affords the desired acids in the form of the corresponding organic or inorganic esters, said esters being generally stable under the reaction conditions for hydrolizing the intermediate iminoethers.

Therefore, the obtain the corresponding free acids it is necessary to submit the above esters to further treatments which may involve acidic or basic hydrolysis, hydrogenolysis or photolysis. These reactions occur generally under quite drastic conditions, which however are disadvantageous with penicillins and cephalosporins owing to the lability of the heterocyclic system. The results of these procedures are thus the formation of unwanted by-products and consequently low overall yields. Blocking of the carboxy group by formation of silyl esters as described in U.S. Pat. Nos. 3,499,909 and 3,575,970 represents a remarkable improvement over the method described in the previously cited U.S. Patent, but has considerable disadvantages as well, which are essentially due to the nature of the protecting agents. In fact the haloalkylsylanes, alkylsilazanes or the analogous silicon derivatives which are employed as protecting groups of the carboxy function according to the two mentioned U.S. Patents must be handled with extreme caution being inflammable substances, and the step concerned with the protection has to be carried out under rigorous anhydrous conditions because they are very moisture-sensitive and are rapidly destroyed by traces of water.

Furthermore, the application on industrial scale of a process involving as the first step of a carboxylic function with silanes or silazanes is not convenient, because the protecting agents are so expensive materials, that the cost of the final products is considerably effected. This is even more true if penicillins or cephalosporins deriving substrates are employed which contain other functions, such as, for instance, amino, hydroxy, sulfhydryl or another group which require protection in order to avoid undesirable side-reactions. This method is therefore not very flexible, as it requires a critical selection of the starting penicillin or cephalosporin substrate. All these drawbacks are removed when, according to the present invention, the carboxy group on the heterocyclic portion of the compounds of formulas I, II and III is reacted with an oxalyl halide, such as, for instance, oxalyl chloride or oxalyl bromide, at a temperature at which oxalyl halides surprisingly act as protecting agents, whereby the carboxy group is transformed into the moiety COO—COCOhal, where hal stands for a halogen atom, preferably bromine or chlorine.

In this case, as well as when the carboxy group is protected as a silyl ester, the free carboxy group is restored simultaneously with the hydrolysis of the intermediate iminoether, being the cleavage of the amidic bond carried out in both instances substantially according to Belgian Pat. No. 628,494. However it must be pointed out that oxalyl halides, unlike haloalkylsilanes, alkylsilazanes and analogous derivatives, are very cheap commercially available products, are easy to handle and offer considerably low risk of causing harm to technicians or workers.

Furthermore, oxalyl halides allow to shorten remarkably the times of the entire process: in fact, the protection of the carboxy groups takes place about at the same temperature of the subsequent steps, while the formation of the silyl esters occurs at room temperature, and a drastic cooling of the reaction mixture is required to perform the other passages. Finally, the processes of this invention can advantageously be carried out on a great variety of starting substrates. These and other advantages which will be apparent from a more detailed description of the invention make the process herein described particularly suitable to be applied on industrial scale, also because the overall yields with which 6-aminopenicillanic acid, 7-aminocephalosporanic acid or its derivatives at the 3-position with various substituents are obtained are generally higher than 95%.

According to a preferred mode of carrying out the process of the invention, the selected substrate of formula I, II or III or an acid salt thereof is dissolved or suspended in an inert organic solvent such as, for instance, diethyl ether, nitromethane, halogenated hydrocarbons containing from 1 to 4 carbon atoms (methylene chloride and chloroform are the most preferred ones), in the presence of an acid binding agent, which is suitably selected from tertiary organic bases, e.g. tri-($C_{1-4}$) alkylamines, N,N-dimethylaniline, quinoline, pyridine, lutidine, picoline and analogs. The presence of the acid binding agent is required both for blocking the acid which derives from the selected substrate if this is used as an acid addition salt, and for binding the hydrohalogenic acid which forms the subsequent step concerned with the protection of the carboxy group by means of oxalyl halides. This step is carried out by rapidly cooling the resulting solution to about −40° C and then adding a molar excess over the starting compounds of formulas I, II or III of the selected oxalyl halide; preferably, oxalyl chloride is used. The amount of the oxalyl halide which is added chiefly depends on the selected starting substrate, since it may contain other functions which must be blocked in order to avoid undesirable side-reactions:these functions are for instance represented by hydroxy, amino, sulfhydryl or even by another carboxy group when a compound is selected where R is the radical

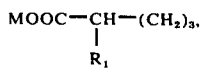

wherein M and $R_1$ are defined as above.

Under the employed reaction conditions oxalyl halides prove to be excellent protective groups also for the above cited functions, which are easily restored at the end of the process simultaneously with the carboxy group. The amount of oxalyl halide which is added is about 2–10 times the molar amount of the selected starting substrate of formula I, II or III.

The two reactants are allowed to contact for 25–40 minutes at a temperature comprised between −10° and −60° C, preferably between −30° and −45° C, then the reaction mixture is submitted to the reaction conditions for cleaving the amidic bond.

This procedure comprises as the first step the reaction with a halogenating agent, at about −30° and −50° C, for one-two hours in the presence of an acid binding agent, which is defined as above. Examples of halogenating agents which can advantageously be employed are phosphorus pentachloride, phosphorus pentabromide, thionyl chloride, phosphorus tribromide, phosphorus oxychloride, phosgene, p-toluenesulfonylchloride. Accordingly, the amidic group of the selected starting compound of formula I II and III is converted into an iminohalide group, which is in turn transformed into the corresponding iminoether by reaction at a temperature between −35° and −50° C with an appropriate primary or secondary alcohol or a ($C_{1-4}$) alkyl orthoformate. Examples of alcohols which can suitably be used are represented by ($C_{1-4}$) alkanols, such as, for instance, methanol, ethanol, propanol, isopropanol, butanol or isobutanol, phenyl ($C_{1-4}$) alkanols, e.g. benzyl alcohol, ($C_{5-7}$) cycloalkanols as, for example, cyclohexanol, or ($C_{2-8}$) alkanediols, e.g. ethylene glycol, 1,6-hexane-diol and analogs. When an orthoformate is used, it is generally ethyl orthoformate.

Also, this step requires to be carried out in the presence of an acid binding agent, which is defined as above. The obtained iminoethers are then poured into a mixture of water/($C_{1-4}$) alkanols and the resulting solution is allowed to stand for about nine-fourteen hours at a temperature between −5° and 10° C. A highly pure crystalline precipitate forms which is recovered by filtration. The compound so obtained, depending on the starting substrate, is 6-aminopenicillanic acid, 7-aminocephalosporanic acid or a derivative of the 3-position of 7-aminocephalosporanic acid. These compounds are recovered in almost quantitative overall yields, in any case never lower than 95%. The following examples are provided with the purpose of better illustrated the preferred emodes of performing the invention, but are not intended to establish any upper limit to the invention itself.

EXAMPLE 1

1 Gram (0.00177 mole) of N-(p-nitrobenzoyl)-cephalosporin C is suspended in 15 ml. of methylene chloride containing 0.25 ml. of triethylamine, then 0.45 ml. of N,N-dimethylaniline are added. The resulting solution is cooled to −40° C, then 1.5 ml. (0.0171 mole) of oxalyl chloride are added dropwise and the resulting mixture is allowed to stand at about −40° C for 30 minutes. After adding 890 mg. of phosphorus pentachloride and 1.1 ml. of N,N-dimethylaniline, the solution is cooled to about −60° C, added with 9.5 ml. (0.0985 mole) of freshly distilled butanol containing 0.2 ml. of N,N-dimethylaniline and kept for 90 minutes at −40° C. The reaction mixture is poured into a mixture of 9 ml. of water and 4.5 ml. of ethanol, then the pH of the resulting solution is brought from the initial value of 0.5 to 3–5 upon adding aqueous 20% ammonium hydroxide. Upon standing overnight at 0°–5° C a crystalline product separates which is filtered, washed with methanol and acetone and dried. Yield: 0.471 g. (98.2%) of 7-aminocephalosporanic acid.

EXAMPLE 2

The process described in Example 1 runs also with cephalosporin C directly isolated from the fermentation broth as N-(p-nitrobenzoate) having a purity degree of 80%. Starting from 1 g. of N-(p-nitrobenzoyl)-cephalosporin C of the indicated purity 0.367 g. (95%) of 7-aminocephalosporanic acid are obtained.

EXAMPLE 3

By operating as in Example 1, starting from 1.6 g. (0.00282 mole) of N-(p-nitrobenzoyl)-cephalosporin C and employing 0.00855 mole of oxalyl chloride, 0.743 g. (97%) of 7-aminocephalosporanic acid are obtained.

EXAMPLE 4

1 Gram of N,(p-nitrobenzoyl)-cephalosporin C with a purity degree of 80% is treated with 0.0171 mole of oxalyl chloride and phosphorus pentachloride as described in Example 1. The reaction mixture is then treated at about −40° C with 4 ml. of ethyl orthoformate containing catalytic amount of aqueous 20% hydrochloric acid instead of butanol and kept at the same temperature for 80–100 minutes. The recovery of the final product is again carried out as in Example 1. Yield 0.375 g. (97.5) of 7-aminocephalosporanic acid.

EXAMPLE 5

The process of Example 1 is repeated starting from 0.915 g. (0.00191 mole) of cephalosporin C zinc salt. The 7-aminocephalosporanic acid is recovered in almost quantitative yields.

EXAMPLE 6

The procedure of Example 1 is repeated starting from 0.930 g. (0.00179 mole) of N-benzoylcephalosporin C. Yield: 0.466 g. (96%) of 7-aminocephalosporanic acid.

EXAMPLE 7

The procedure of Example 1 is repeated by using as the substrate 1.09 g. (0.00178 mole) of N-(p-nitrobenzoyl)-cephalosporin C disodium salt. Yield: 0.490 g. (almost quantitative yield) of 7-aminocephalosporanic acid.

EXAMPLE 8

The procedure of Example 1 is repeated starting from 1.65 g. (0.00221 mole) of N-(p-nitrobenzoyl)-cephalosporin C di-cyclohexylamine salt. Yield: 0.578 g. (96.5%) of 7-aminocephalosporanic acid.

EXAMPLE 9

The procedure of Example 1 repeated starting from 2 g. (0.00562 mole) of benzylpenicillin sodium salt. Yield: 1.178 g. (97%) of 6-aminopenicillanic acid.

We claim:

1. In a process for preparing 6-aminopenicillanic acid, 7-aminocephalosporanic acid and derivatives at the 3-position of 7-aminocephalosporanic acid, said compounds being represented by the following general formula

[structure: $H_2N$-β-lactam-$D^1$]

wherein $D^1$ may be the group

[structure: $C(CH_3)_2$-CH(COOH)-]

or the group

[structure: $=C(CH_2-)C(COOH)=CH-CH_2-X$]

in which the carbon atom bearing the carboxy group is linked to the nitrogen atom of the β-lactam ring, and in which X represents hydrogen, hydroxy, sulfhydryl, halo, azido, cyano, $(C_{1-6})$ alkyl, $(C_{2-6})$-alkanoyloxy, carbamoyloxy, $(C_{1-6})$ alkylcarbamoyloxy, aryloxy, aralkyloxy, aroyloxy, arylalkanoyloxy wherein the aromatic portion is represented by a phenyl or naphthyl radical optionally substituted with $(C_{1-4})$ alkyl, $(C_{1-4})$-alkoxy, halo and nitro groups and the alkyl or alkanoyl portions contain from 1 to 4 carbon atoms, tri-$(C_{1-4})$-alkylammonio, pyridinio, $(C_{1-4})$ alkyl-substituted pyridinio, an —S—Y or $$-S-\overset{\overset{O}{\|}}{C}-Y \text{ group}$$

wherein Y represents $(C_{1-6})$ alkyl, $(C_{2-6})$ alkanoyl, aryl and aralkyl as above defined, a 5-7 membered heterocyclic ring containing O, N and S and optionally substituted with $(C_{1-4})$ alkyl, hydroxy, hydroxy $(C_{1-4})$ alkyl or trifluoromethyl, selected from the group consisting of thiazole, isothiazole, oxazole, isooxazole, 1,3,4-thiadiazole, 1,2,4-thiadiazole, 1,2,5-thiadiazole, 1,3,4-oxadiazole, 1,2,3-oxadiazole, 1,2,5-oxadiazole, 1,2,4-triazole, 1,2,3-triazole, tetrazole, pyridine, pyridazine, purimidine and pyrazone, the improvement which comprises reacting a molar proportion of a substrate of the formula

[structure: R—CO—NH-β-lactam-D]

or an acid salt thereof, wherein R is selected from:
a. an alkyl group of 2 to 8 carbon atoms;
b. a $$\text{MOOC}-\underset{\underset{R_1}{|}}{CH}-(CH_2)_3 \text{ group}$$

wherein M is hydrogen or metal or ammonium cations and $R_1$ is hydrogen, amino or a protected amino group;
c. a

[structure: phenyl—W—$(CH_2)_m$ group]

wherein W represents O, S or a carbon-carbon bond, and m is an integer from 0 to 3, with the proviso that when W is oxygen or sulfur, m is different from zero;
d. a

[structure: phenyl with $R_5$, $R_6$ substituents—CH(Q)—]

wherein Q represents hydrogen, hydroxy or amino and $R_5$ and $R_6$ are independently selected from hydrogen, hydroxy, amino and halo;

e. a

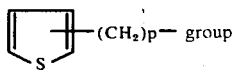 group wherein $p$ is an integer 1 to 3; D is the group

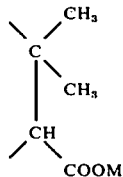

or the group

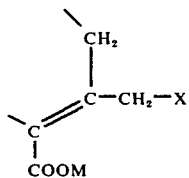

in which the carbon atom bearing the COOM group is linked to the nitrogen atom of the β-lactam ring and M and X are as above defined, with a molar excess of an oxalyl halide of formula halCOCOhal, wherein hal stands for a halogen atom, in an organic solvent, in the presence of an acid binding agent, at a temperature comprised between about −10° and about −60° C, for 25 to 40 minutes, whereby the —COOM group is transformed into the group COO——COCOhal in which hal is as above defined, treating the obtained compound with a halogenating agent selected from phosphorus pentachloride, phosphorus pentabromide, thionyl chloride, phosphorus tribromide, phosphorus oxychloride, phosgene and p-toluenesulfonylchloride at a temperature comprised between about −30° and about −50° C, in the presence of an acid binding agent for one to two hours and subsequently with a ($C_{1-4}$) alkyl orthoformate or an alcohol selected from ($C_{1-4}$) alkanols, phenyl($C_{1-4}$) alkanols, ($C_{5-7}$) cycloalkanols and ($C_{2-8}$) alkanediols, at a temperature ranging between about −30° and −50° C, in the presence of an acid binding agent, and hydrolyzing the otained iminoether in a mixture of water and a ($C_{1-4}$) alkanol, for about nine to about 14 hours, at a temperature between about −5° and 10° C, at an acidic pH comprised between about 3 and about 5.

2. A process as in claim 1, wherein the protecting group of the amino function is selected from acyl radicals driving from mono- or di-carboxylic acids of 2 to 8 carbon atoms optionally substituted with halogen atoms, benzoyl, phenyl and benzoyl carrying 1 to 3 substitutents independently selected from halo, nitro and cyano, phenacetyl, benzyloxycarbonyl, tert-butoxycarbonyl, ($C_{5-7}$) cycloalkyloxy carbonyl, benzenesulfonyl, toluenesulfonyl, phenacylsulfonyl, a group representable by the formula

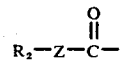

wherein Z is O or NH and $R_2$ is ($C_{1-6}$) alkyl or the group

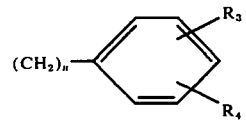

where $n$ is an integer from 0 to 6 and $R_3$ and $R_4$ independently represent hydrogen, halogen, nitro, ($C_{1-6}$) alkyl, ($C_{1-6}$) alkoxy.

3. A process as in claim 1, wherein from about 2 to about 10 molar equivalents of the oxalyl halide are employed for each molar equivalent of the compound of formula I.

4. A process as in claim 3, wherein the oxalyl halide is oxalyl chloride.

5. A process as in claim 1, wherein the organic solvent is a lower halogenated hydrocarbon.

6. A process as in claim 5, wherein the lower halogenated hydrocarbon is methylene chloride.

7. A process as in claim 1, wherein the acid binding agent is a ($C_{1-4}$) alkylamine, N,N-dimethylaniline or a mixture thereof.

8. A process as in claim 1, wherein the reaction between the oxalyl halide and the substrate of formula I is carried out at a temperature comprised between about −35° and about −45° C.

9. A process as in claim 1, wherein the halogenating agent is phosphorus pentachloride.

10. A process as in claim 1, wherein the ($C_{1-4}$) alkyl-orthoformate is ethyl-orthoformate.

11. A process as in claim 1, wherein the employed alcohol is an aliphatic alcohol containing from 1 to 4 carbon atoms.

12. A process as in claim 11, wherein the aliphatic alcohol is butanol.

13. In a process for preparing a compound of the formula

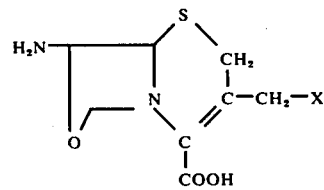

wherein X is defined as in claim 1, which comprises reacting a molar amount of a substrate of formula

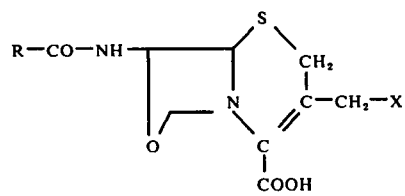

or an acid salt thereof, wherein R, X and M are defined as in claim 1, with 2 to 10 molar equivalents of oxalyl chloride, in methylene chloride, in the presence of a mixture of triethylamine and N,N-dimethylaniline at a temperature comprised between about −35° and −45° C, for 25 to 40 minutes, treating the obtained product with phosphorus pentachloride at a temperature between about −30° and about −50° C in the presence of N,N-dimethylaniline for 1 to 2 hours and subsequently with an agent selected from ethyl orthoformate and butanol at a temperature comprised between about −30° and about −50° C, in the presence of N,N-dimethylaniline, and hydrolyzing the obtained iminoether in a mixture of water and ethanol, for about 9 to about 14 hours, at a temperature between about −5° and about 10° C, at an acidic pH comprised between about 3 to about 5.

14. A process as in claim 12, whereby 6-aminopenicillanic acid of formula

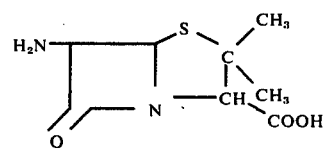

is prepared starting from a substrate of formula

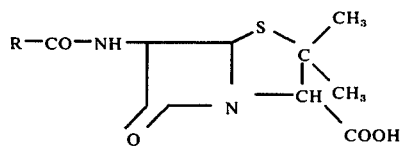

or an acid salt thereof, wherein R and M are as above defined.

* * * * *

UNITED STATES PATENT AND TRADEMARK OFFICE
CERTIFICATE OF CORRECTION

PATENT NO. : 4,021,426  
DATED : May 3, 1977  
INVENTOR(S) : Ernesto Oppici and Anacleto Gianantonio Page 1 of 2

It is certified that error appears in the above-identified patent and that said Letters Patent are hereby corrected as shown below:

Column 1, the formula between lines 60 and 65 should read:

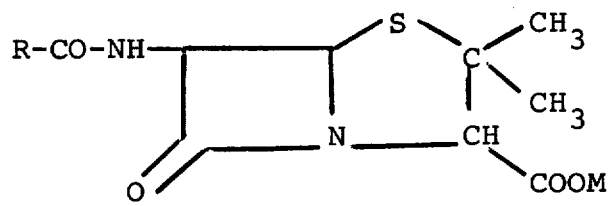

Column 4, line 7, "substitutents" should read -- substituents --

Column 4, line 28, "wherein" should read -- where --.

Column 4, line 63, "steps" should read -- step --.

Column 5, line 65, "Therefore, the" should read
                -- Therefore, to --.

Column 8, line 13, "derivative of" should read
                -- derivative at --.

Column 8, line 18, "ter illustrated the preferred emodes"
should read       -- ter illustrating the preferred modes --.

Column 9, EXAMPLE 9, first line, "Example 1 repeated"
should read                    -- Example 1 is repeated --.

UNITED STATES PATENT AND TRADEMARK OFFICE
CERTIFICATE OF CORRECTION

PATENT NO. : 4,021,426
DATED : May 3, 1977
INVENTOR(S) : Ernesto Oppici and Anacleto Gianantonio It is certified that error appears in the above-identified patent and that said Letters Patent are hereby corrected as shown below:

Column 10, line 4, "$(C_{1-6})$ alkyl," should read -- $(C_{1-6})$ alkoxy, --.

Column 10, line 27, "purimidine" should read -- pyrimidine --.

Column 10, between lines 60 and 65, following the formula, the omitted word "group" should be inserted.

Column 11, line 54, "otained" should read -- obtained --.

Column 11, line 61, "cals driving" should read -- cals deriving -

Column 11, line 64, "substitutents" should read -- substituents --.

Signed and Sealed this

First Day of November 1977

[SEAL]

Attest:

RUTH C. MASON
*Attesting Officer*

LUTRELLE F. PARKER
*Acting Commissioner of Patents and Trademark*